United States Patent
Hui

(10) Patent No.: US 8,252,155 B2
(45) Date of Patent: Aug. 28, 2012

(54) ELECTROLYTIC CELL FOR GENERATING CHLORINE IN A POOL

(75) Inventor: Wing-kin Hui, Hong Kong (HK)

(73) Assignee: Heavy Gain Limited, Hong Kong (HK)

( * ) Notice: Subject to any disclaimer, the term of this patent is extended or adjusted under 35 U.S.C. 154(b) by 0 days.

(21) Appl. No.: 12/551,127

(22) Filed: Aug. 31, 2009

(65) Prior Publication Data

US 2011/0253527 A1    Oct. 20, 2011

(51) Int. Cl.
  *C25B 9/06* (2006.01)
  *C25B 1/24* (2006.01)
  *C02F 1/461* (2006.01)
  *C02F 1/467* (2006.01)

(52) U.S. Cl. .................... 204/278.5; 210/748.2

(58) Field of Classification Search .......... None
  See application file for complete search history.

(56) References Cited

U.S. PATENT DOCUMENTS

| | | | | |
|---|---|---|---|---|
| 3,822,017 A | * | 7/1974 | Rast | 210/145 |
| 4,923,582 A | * | 5/1990 | Abrahamson et al. | 204/255 |
| 5,039,383 A | * | 8/1991 | Spotnitz et al. | 205/618 |
| 5,108,563 A | * | 4/1992 | Cook | 205/688 |
| 5,326,443 A | * | 7/1994 | Hilbig | 210/97 |
| 5,897,757 A | * | 4/1999 | Sano | 204/284 |
| 6,007,693 A | * | 12/1999 | Silveri | 205/335 |
| 7,014,753 B2 | * | 3/2006 | Holstein et al. | 210/136 |
| 7,374,645 B2 | * | 5/2008 | Davis et al. | 204/242 |
| 2002/0074237 A1 | * | 6/2002 | Takesako et al. | 205/628 |
| 2007/0007146 A1 | * | 1/2007 | Childers et al. | 205/501 |
| 2007/0251830 A1 | * | 11/2007 | Conrad | 205/508 |
| 2010/0213049 A1 | * | 8/2010 | Burtch | 204/242 |

\* cited by examiner

Primary Examiner — Harry D Wilkins, III
(74) Attorney, Agent, or Firm — Peninsula IP Group; Douglas Chaikin

(57) ABSTRACT

Disclosed herein is an improved electrolytic cell. The cell includes at least one pair of electrodes, an anode and a cathode. In general the anode includes at least one dimension, which is substantially greater than the cathode. In an exemplary embodiment, the length and the width of the anode are greater than the length and width of the cathode. In a first embodiment of a multi-cell chlorine generator, unequal dimension electrodes are stacked together. In a second embodiment of such a generator, the electrodes are of equal dimensions. In another exemplary embodiment of the improved electrolytic cell in accordance with this invention, the cathode forms a U-shaped member and the anode of at least one dimension being greater is located there between. Another embodiment of the chlorine generator includes at least two cells having the U-shaped cathode. In a first exemplary of embodiment of such a chlorine generator, the electrode are parallel to one another. In a second such exemplary embodiment, the electrodes are parallel and are coincident in plane with one another, respectively.

8 Claims, 4 Drawing Sheets

ELECTROLYTIC CELL FOR GENERATING CHLORINE IN A POOL

RELATED PATENT APPLICATIONS

This application is relates to three other of Applicant's filings, which are filed concurrently with this application. Those filings are. Ser. Nos. 12/551,211, 12/551,185 and 12/551,098 Upon receiving serial numbers for all three cases, Applicant will amend this section of the application to include those serial numbers. Additionally, each of those applications is specifically incorporated in full in this application, as if they were word for word written here. They are incorporated in full for all purposes.

FIELD OF THE INVENTION

This invention generally relates to the field of automated pool products. More particularly, this invention relates to electrolytic cells used for generating chlorine for a swimming pool and for doing so in an automatic fashion.

BACKGROUND OF THE INVENTION

Chlorine or ion generation for a swimming pool has long been known as being useful for healthful and safe swimming. For example, chlorine mixed water is required of most municipal and public swimming pools in the United States and Canada. The chlorine level must be carefully regulated and adjusted if necessary in such public swimming pools to provide swimmers, including small children with a safe and healthful place to bath and swim.

Manual methods of adding chlorine to the swimming water are well known. The pool attendant take precautions to not get the chlorine directly on him/herself and then adds the proper amounts to the pool water. Various tests are done to the pool water to see ensure the proper concentration levels of chlorine are present. It is also well known that other ion elements are used to treat pool water. For example, bromine, is also used in a similar to chlorine for safely cleaning pool water.

For many years, automated chlorinators have been known. The known automated chlorinators include means for testing the pool water to determine whether or not the appropriate level of chlorine or other ion mixed in the water is present. For example, generally speaking, the testers look for levels of 2700 ppm. When the level drops below that level the automated chlorinator is activated and adds chlorine or other ion to the water, increasing the level until the 2700 ppm is reached.

These chlorinators can be very expensive. For example, a common automated chlorinator can cost the consumer upwards of several thousands of dollars. Additionally, these expensive chlorinators are somewhat fragile and often need expensive repairs or even replacement.

In fact, the general thinking has been to make the coated anode smaller. The coating is an expensive process and consequently the conventional thinking has been to make the coated anode as small as possible. As will be described herein, Applicant's theory of the invention is not only a departure from structure, but also from conventional thinking.

U.S. Pat. No. 7,014,753 entitled Salt Chlorine Generator is specifically incorporated herein for all purposes, including, but not limited to it use as Background, antecedent basis and as a reference and an example of previously known devices. One of the inventors therein, then known as Joseph Hui, is the inventor herein.

At the heart of the modern automated chlorinator is an electrolytic cell. A typical such cell includes two electrodes, an anode and a cathode in a salt solution as described above with respect to the '753 patent. Once electrical power is applied to the electrodes, a chemical reaction begins. In a salt (NaCl) solution, the CI is stripped out and floats freely in the water, safely cleaning the pool water.

Point/Edge Effect:

It is well known that there is a higher electrical potential at the edges of an electrodes than anywhere else. These edges or points as they are sometimes known tend to deteriorate faster than any where else on the electrode. The result is, of course, premature wear of the electrode. It is well known that first failure of the electrode occurs at the edge, in fact, at the point edge. Eventually, the electrode or perhaps the entire chlorinator needs to be replaced earlier than it should.

The point/edge effect leads to spotting or patches being created in the coating of the electrodes. The greater the current that is generated by the cell, the faster such spotting will spread and the quicker the coating will be lost and the more rapid the destruction of the electrode.

Clearly, by preventing the starting of the degradation at the point edge of the electrode, the longevity will dramatically be increased. If the pressure of the electrical activity on the point edge is decreased, the pressure on the electrode will be decrease, again extending the longevity of the electrode.

What is needed is an inexpensive automated chlorinator, which does not require expensive repair and which is reliable and can fit existing pool configurations.

SUMMARY OF THE INVENTION

The structure, in accordance with the present invention, is an electrolytic cell having a particular construction. In one embodiment, the cell includes two electrodes, an anode and a cathode. In this embodiment, the dimensions of the anode exceed, at least in one respect, one of the dimensions of the cathode. In another embodiment both the length and width of the anode exceed the length and width of the cathode.

Another exemplary embodiment in accordance with the invention features, several pairs of electrodes or cells stacked together. In this configuration, each of the electrodes forms plates and each of the plates is parallel to another. In one exemplary embodiment, the cell described above, wherein at least one dimension of the anode exceed the correspondingly dimension of the cathode is used as the stacking cell. In another exemplary embodiment of the stacking electrolytic cell embodiment, the electrode plates are not only parallel, but, in addition, the electrode plates are coincident, meaning that the anode of cell 1 lies in the same plane as the anode of cell 2 and the cathode of cell 1 lies in the same plane as the cathode of cell 2.

Thus, it is an object of this invention is to provide an electrolytic cell having a unique construction, which encourages efficient operation and reliable service and inexpensive construction.

It is another object of this invention to provide an electrolytic cell in accordance with this invention, which can be stacking together with other similar cells and form a larger cell having greater voltage.

It is an additional object of this invention to provide such a single or stacked cell that is readily adapted for use in a pool environment for producing Chlorine or other ion elements for safely and effectively cleaning pool water.

In another exemplary embodiment of the electrolytic cell in accordance with the invention, the cathode forms a U-shaped configuration and the anode fits between the side walls.

In other exemplary embodiments, at least one of the electrodes is made from a semi-conductor material. One such material is titanium. In another exemplary embodiment, at least one electrode is coated with corrosion resistant material, for example, platinum or palladium.

In accordance with the objects set forth above and as will be described more fully below, the electrolytic cell in accordance with this invention, comprises:

at least one cell, the cell including two electrodes, an anode and a cathode;

the cathode having a predetermined length and width;

the anode having a predetermined length and width and at least one of the said dimensions extending beyond the cathode;

whereby the anode physically extends beyond the cathode, while the electrolytic cell generates chlorine in an ion-aqueous solution.

In another exemplary embodiment, the space between cells is greater than the space between electrode plates. It has been found where the plates form the electrodes that short circuit is discouraged by such a configuration.

By extending the anode, the area of electrical activity is increased. By increasing the area of electrical activity, the electrical pressure is spread over the greater area, also discouraging point/edge degradation.

It is an advantage of the electrolytic cell in accordance with this invention to provide such a cell which has the ability to provide chlorine into a pool for safe and effective cleaning of the pool water.

It is an additional advantage of the device of the instant invention to provide a multi-cell electrolytic device having additional voltage and providing a greater voltage than a single cell embodiment.

The multi-cell device is readily adaptable for use as a chlorine generator for treating pools of greater capacity.

BRIEF DESCRIPTION OF THE DRAWING

For a further understanding of the objects and advantages of the present invention, reference should be had to the following detailed description, taken in conjunction with the accompanying drawing, in which like parts are given like reference numerals and wherein.

DETAILED DESCRIPTION OF THE INVENTION

In order to appreciate the invention herein, one must appreciate the need in the art as set forth in the Background. Most importantly, the structure herein for resolving the long felt need to increase the efficiency and durability in the area of pool cleaning devices, such as pool chlorinators are represented by the structure in accordance with the disclosed invention.

Figure 1:
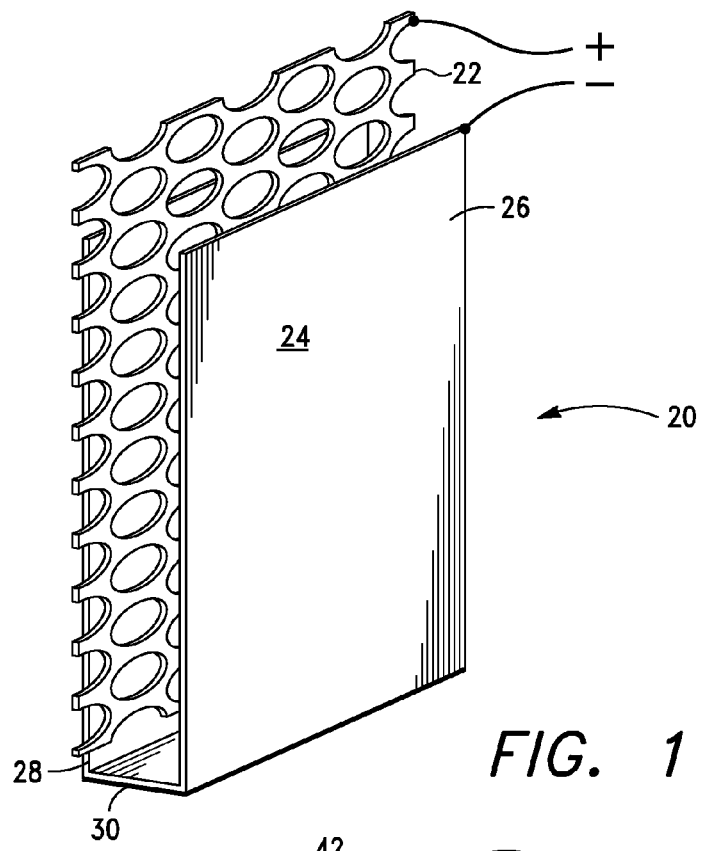
FIG. 1 is a perspective view of an electrolytic cell in accordance with this invention having a U-shaped cathode and with the anode extending in at least one dimension.

An exemplary embodiment of the electrolytic cell which is adaptable for use in a chemical pool cleaner is illustrated in FIG. 1 and generally denoted by the numeral 20. Illustrated in FIG. 1 is the exemplary embodiment that includes two electrodes, an anode 22 or a cathode 24. The anode 22 has a predetermined length and width. Likewise, the cathode 24 has a predetermined length and width. An important aspect of the invention is that at least one dimension of the anode exceeds that of the cathode 24. Illustrated in FIG. 1 is the exemplary embodiment where both the length and width of the anode 22 exceeds that of the cathode 24.

The anode 22 is in the form of a waffle plate or mesh.

Figure 7:
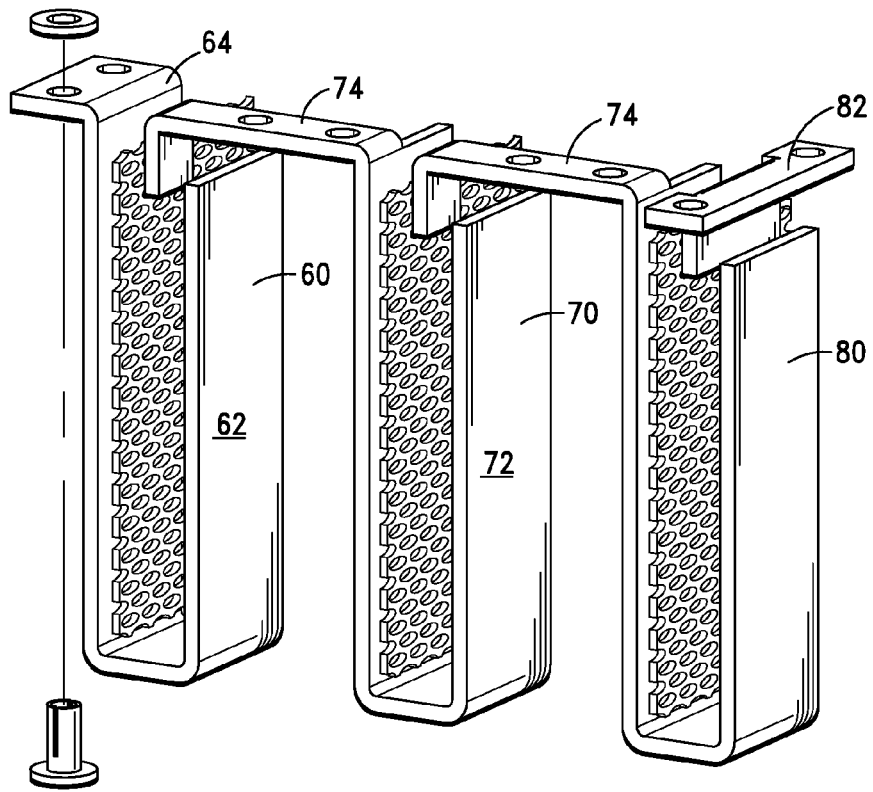
FIGS. 7 & 8 are stacked cell embodiment illustrated construction in preparation for connection to a water chlorinator.
Figure 8:
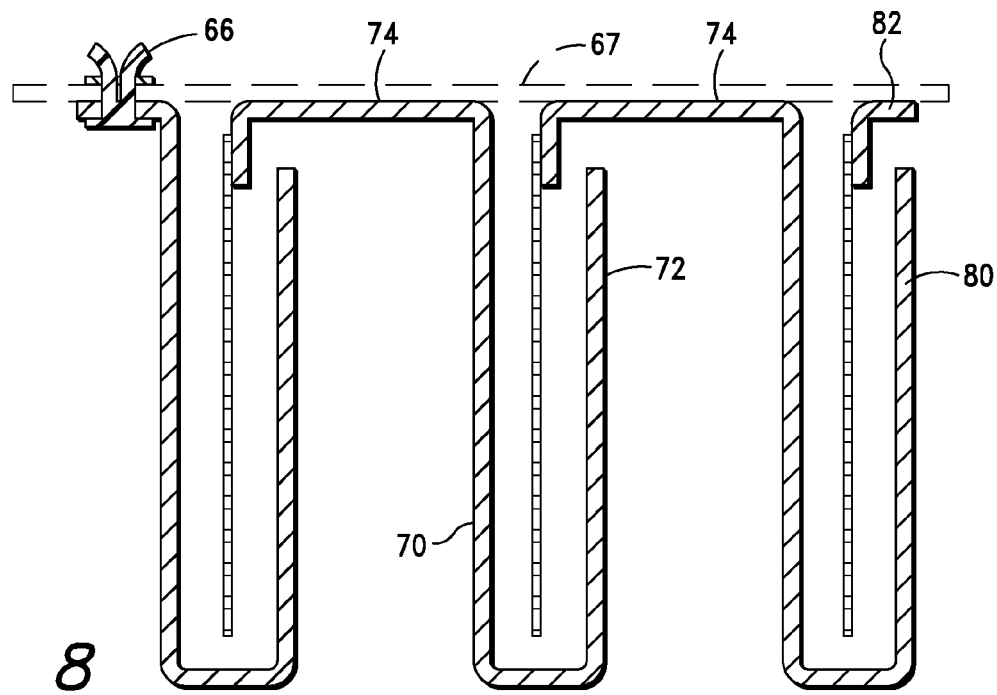

Additionally, illustrated in FIG. 1 is the embodiment where the cathode 24 is U-shaped. In this embodiment, the cathode 24 includes a first upstanding wall 26 and a second upstanding wall 28. A joining member 30 extends between the walls 26 and 28. The anode 22 fits between the upstanding walls 26 and 28. FIGS. 7 and 8 illustrate an exemplary embodiment of a chemical cleaning device in accordance with this invention, in particular, a chlorinator including the U-shaped embodiment. As explained below, the electrolytic cell discussed is particularly useful in such a device.

It will be appreciated that only one dimension of the cathode 24 needs to be exceeded by the anode. Described above is the embodiment where both length and height are exceeded by the anode. This is not to be limiting of the invention.

In the exemplary embodiment described above, the length and width of the anode exceeds the cathode by 0.5 cm. In other embodiments, the length and width of the anode may exceed the cathode by up to 2 cm.

It will be appreciated by those skilled in the art that by extending the dimensions of length and width of the anode, the uneven electrical field at the points and edges is minimized, thus nullifying the point/edge effect. The extended dimensions of the anode compensate for the point edge effect by equalizing the uneven electrical field.

Additionally, there is less resistance and less loss with the above described configuration of the anode. This results in three immediate advantages. First, the power supply can be reduced that supplies electricity to the electrodes. Second, the same size cell generates greater amounts of chlorine (or any halogen) to the pool environment, thereby increasing the efficiency of the cell. Thirdly, when the point/edge is minimized, the cell in accordance with this invention runs at a higher average current density.

Materials and Coating

It has been found that forming at least one of the electrodes from an inert metal material such at Titanium prolongs the lifespan of the entire cell. Additional beneficial properties are found when at least one of the electrodes is made from platinum or coated with platinum. These properties include corrosion resistance and malleabilty.

Using noble metals for anode which generate chlorine by electrolysis results in resistance to corrosion and low electrical resistance. By using such noble metals overall electrolysis efficiency is improved Additionally, when at least one of the electrodes is coated with a multi-metal oxide such as Ruthenium anode similar advantages result. However, because the anode is wider then the U-shaped cathode and because such a coating is relatively expensive, in the preferred embodiment, only the anode is coated with the Ruthenium in accordance with the principles set forth above and in contravention of current thinking.

Additionally it has been found that coating at least one of the electrodes with a corrosive resistant material such as platinum or palladium also prolongs the life the electrodes.

Figure 2:
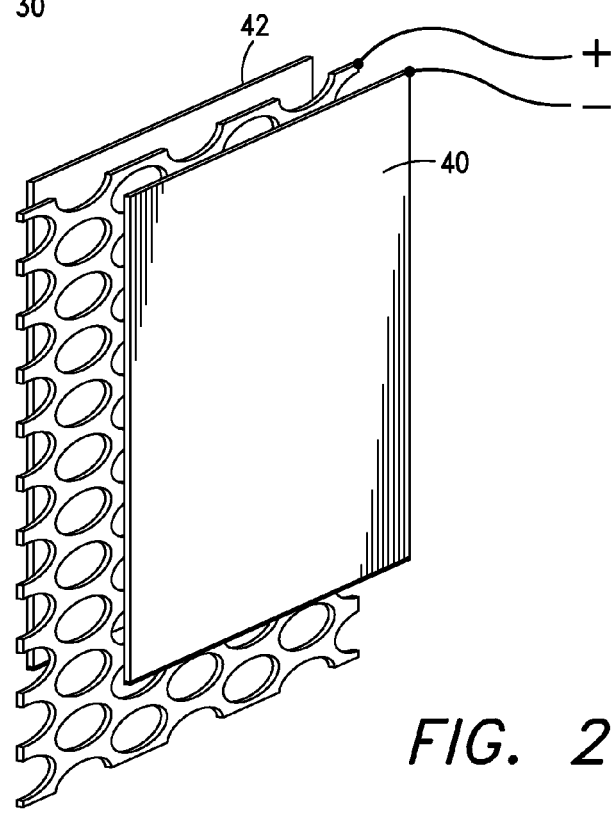
FIG. 2 is a perspective view of an electrolytic cell in accordance with this invention having plate electrodes with the anode extending in at least one dimension.

FIG. 2 illustrates another exemplary embodiment of the electrolytic cell in accordance with this invention. This embodiment is known as the plate embodiment. Unlike the U-shaped cathode 24, here the cathode electrode defines two plates 40 and 42. Sandwiched between the two plates 40 and 42, respectively, is the anode 22. Similar to the configuration presented with respect to FIG. 1, the length and width of the anode 22 extend beyond the length and width of the cathode electrode. Specifically, the length and width of the anode 22 exceeds the length and width of the plates 40 and 42.

In the exemplary embodiment shown in FIG. 2, the plates 40 and 42 are identical. However, it will be appreciated by those skilled in the art that such is not necessary. Additionally, all of the coatings and materials preferences described above with respect to FIG. 1 are equally applicable to the exemplary embodiment shown in FIG. 2.

Figure 3:
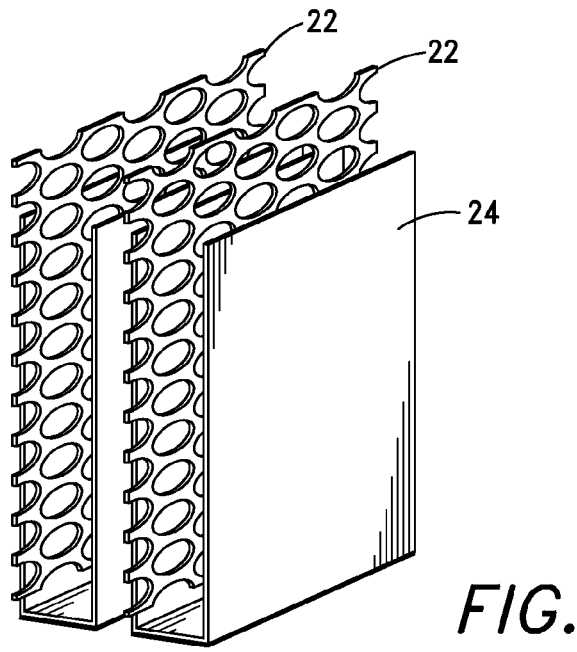
FIG. 3 is a perspective view of the stacked electrolytic cell in accordance with this invention having U-shaped cathodes and with the anodes extending in at least one dimension.
Figure 4:
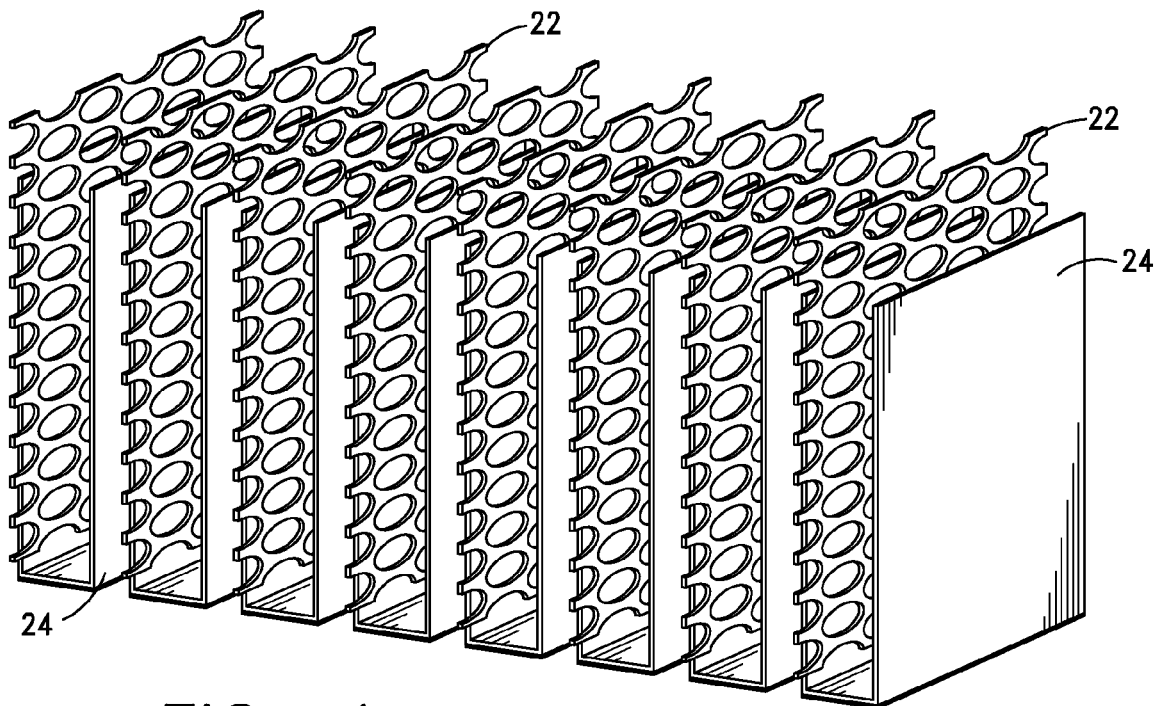
FIG. 4 is a perspective view of another stacked embodiment, employing 8 cells, each having a U-shaped cathodes.

Stacking:

FIG. 3 illustrates a 2-cell side-by-side parallel non-coplanar alignment embodiment, while FIG. 4 illustrates the same type of configuration in an 8-cell embodiment. Each of the cathodes 24 defines a U-shaped cathode 24 as set forth in FIG. 1. Each individual cell includes a second electrode, an anode 22. This embodiment utilizes the same configuration as that described above with reference to FIG. 1.

Using this configuration the electrical output is doubled over the embodiment shown in FIG. 1. Thus, if the cell in FIG. 1 provides a 2 volt capacity, the cell in FIG. 3 provides a 4 volt capacity. Similarly, the cell embodiment shown in FIG. 4 provides 8 times the electrical capacity as that of FIG. 1 or 16 volts.

In the embodiments shown in FIGS. 3 & 4, the plates of the electrodes are all parallel to one another and non-coplanar. Additionally, the cells are oriented and spaced apart in order to prevent a short circuit. In the configuration, shown in FIGS. 3 & 4, the cathode between the cells serves a barrier to prevent such short circuiting. In addition, by placing the cells apart from one another a distance greater than the space between the electrodes, short circuiting is also minimized.

The cells may be connected in either series or parallel. In series the effect of stacking is most pronounced. By stacking in series, the input voltage to the cell is high, while current flow is low for the same power consumption. The power loss between power supply to the halogen generating module as well as power supply itself is greatly reduced. As is understood, the power loss is proportional to the square of current.

Often times when there are more than two anodes in an electrical system such as those described above, a leak path will be created. In FIG. 3, this would mean that under common electrical circumstances, a leak path would be created across the two anodes 22. However, the cathode of each cell is made of a semi-conductor material, such as titanium, which minimizes such a leak path. In order to have current leaks from one cell to the other cell, the cathode of higher potential cell has to act as anode relative to the cathode of the lower potential cell. Semiconductor metal such as titanium does not allow the electrode to act as anode and therefore current can not flow through the 2 adjacent cathodes. Thus, there is no leak path. It will also be appreciated that the anodes may either be made from or coated with platinum or other noble materials within the spirit and scope of the invention. Additionally, the cathode 24 between the anodes 22 also serves as a block for leak paths.

Figure 5:
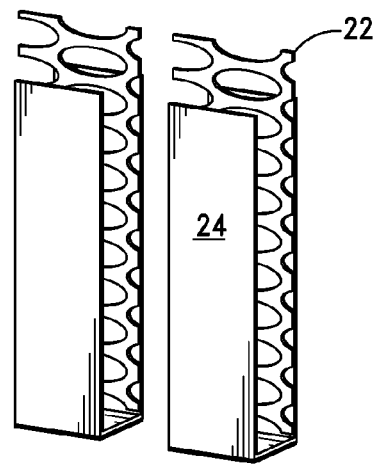
FIG. 5 is a side plan of a staked embodiment of the electrolytic cell in accordance with this invention, illustrating the electrodes being both parallel and coincident.
Figure 6:
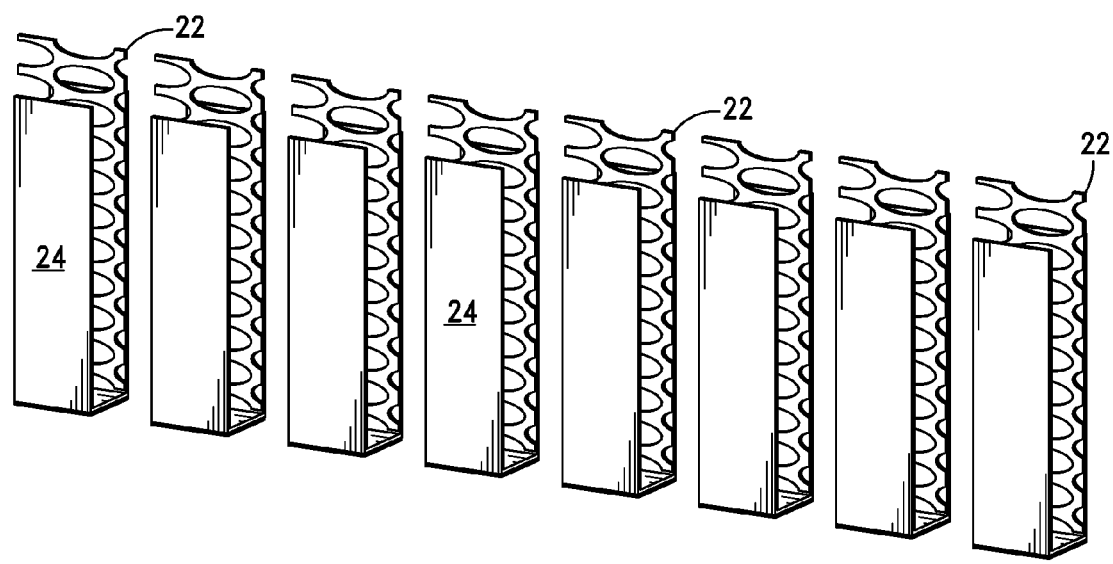
FIG. 6 is an 8 cell embodiment of the stacked electrolytic cell illustrated in FIG. 5.

In the exemplary embodiments illustrated by FIGS. 5 & 6, the electrodes are parallel and co-planar. Each of the electrodes 22 and 24 are side-by-side, parallel and co-planar.

Similar to the embodiments described with respect to FIGS. 3 & 4, the multi-cell embodiments of FIGS. 5 & 6 deliver greater electrical output compared with a single cell. Again, the 2 cell embodiment of FIG. 5 delivers 4 volts and likewise, the embodiment in FIG. 6 delivers 16 volts of electrical potential.

Similar to the multi-cell embodiments described above, the anodes are coated with a noble metal, such as platinum or palladium, which minimizes such a leak path. It will also be appreciated that the anodes may either be made from or coated with titanium or other semi-conductor materials within the spirit and scope of the invention. Additionally, the cathode 24 between the anodes 22 also serves as a block for leak paths.

The cells may be connected in either series or parallel. In series the effect of stacking is most pronounced. By stacking in series, the input voltage to the cell is high, while current flow is low for the same power consumption. The power loss between power supply to the halogen generating module as well as power supply itself is greatly reduced. This assumes each cell has similar electrical characteristics, such as electrical resistance as in the exemplary embodiment. If this is not the case, one cell may run at a higher voltage, while the other cell will run at a lower voltage. By stacking in parallel, unequal cell characteristic do not affect the operating voltage, but current draw is high for the same power consumption, Equipment cost tends to be somewhat higher because the entire system has higher electrical loss.

In Use:

A single cell or multi-cell embodiment is placed in a NaCl aqueous solution. It will be appreciated that other solutions are possible. For example, halogen compound solutions including potassium chloride or sodium bromide are workable.

With respect to FIGS. 7 and 8, there is shown a 3-cell embodiment, connected in series. Cell 1 designated by the numeral 60 includes a U-shaped cathode 62 having a flange 64. Cell 1 includes attachment member 66, which threads through an opening 68 in the flange 64. The attachment member 66 connects the wall of the container 67 for the solution with the electrodes. An anode 22 made of titanium mesh is sandwiched between the U-shaped walls of the cathode 62.

Cell 2 70 includes a second U-shaped cathode 72, also having a flanged end 74. Attached to the flanged end 72 is the anode 22 of Cell 1. Similarly, Cell 3 80 has a flanged end 72 for holding the anode 22 of Cell 2 sandwiched between the U-shaped walls of the cathode 70. Cell 3 like, Cell 1 has a flange 82 for attachment to the container 67 holding the solution.

Thereby, the cell structure is secured to the container and may be placed in use to generate chlorine or other ionizing elements.

While the foregoing detailed description has described several embodiments of the pool cleaning vehicle in accordance with this invention, it is to be understood that the above description is illustrative only and not limiting of the disclosed invention. Thus, the invention is to be limited only by the claims as set forth below.

What is claimed is:

1. An electrolytic cell for the production of chlorine in an ion aqueous solution, the electrolytic cell, comprising:
   at least one cell, the cell including two electrodes, an anode and a cathode;

the cathode having a predetermined length and width, the cathode forms a U-Shape including extended walls;
a joining member;
the anode having a predetermined length and width and at least one of the said dimensions extending beyond the cathode and wherein the anode is located between the extended walls and the joining member;
whereby the anode physically extends beyond the cathode, while the electrolytic cell generates chlorine in an ion-aqueous solution.

2. An electrolytic cell as set forth in claim 1, wherein the ion-aqueous solution comprises a salt water solution.

3. An electrolytic cell as set forth in claim 1, wherein the both the length and the width of the anode extend beyond the length and width of the cathode.

4. An electrolytic cell as set forth in claim 1, wherein there are a plurality of cells stacked together.

5. An electrolytic cell as set forth in claim 4, wherein each of the electrodes stacked are parallel.

6. An electrolytic cell as set forth in claim 4, wherein each of the stacked electrodes are parallel and also lie in the same plane.

7. An electrolytic cell as set forth in claim 1 wherein there are a plurality of cells stacked together in parallel.

8. An electrolytic cell as set forth in claim 1, wherein there are a plurality of cells stacked together in series.

* * * * *